(12) United States Patent
Wentland

(10) Patent No.: US 7,262,298 B2
(45) Date of Patent: Aug. 28, 2007

(54) 4-HYDROXYBENZOMORPHANS

(75) Inventor: Mark P. Wentland, Menands, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 20 days.

(21) Appl. No.: 11/266,651

(22) Filed: Nov. 3, 2005

(65) Prior Publication Data

US 2006/0111384 A1    May 25, 2006

Related U.S. Application Data

(60) Provisional application No. 60/625,348, filed on Nov. 5, 2004.

(51) Int. Cl.
*C07D 221/22* (2006.01)
*A61K 31/439* (2006.01)
(52) U.S. Cl. .................. 546/74; 514/289; 546/75
(58) Field of Classification Search .............. 546/74, 546/75; 514/289
See application file for complete search history.

(56) References Cited

U.S. PATENT DOCUMENTS

| | | | | |
|---|---|---|---|---|
| 3,957,793 | A | 5/1976 | Wentland | 260/293.54 |
| 4,032,529 | A | 6/1977 | Wentland et al. | 260/293.54 |
| 4,205,171 | A | 5/1980 | Albertson | 546/97 |
| 4,373,139 | A | 2/1983 | Beesley | 424/260 |
| 4,649,200 | A | 3/1987 | Portoghese et al. | 546/26 |
| 6,784,187 | B2 | 8/2004 | Wentland | 514/282 |
| 2003/0187009 | A1 | 10/2003 | Wentland | |
| 2005/0215799 | A1 | 9/2005 | Wentland et al. | |

FOREIGN PATENT DOCUMENTS

| | | |
|---|---|---|
| EP | 0632041 | 1/1993 |
| EP | 1359146 | 11/2003 |
| WO | WO97/25331 | 7/1997 ........... 491/12 |

OTHER PUBLICATIONS

Wentland et al. "3-Carboxamido Analogues of Morphine and Naltrexone: Synthesis . . . " Biorg. Med. Chem. Ltrs. 11, 1717-1721 (2001).
Wentland et al. "8-Carboxamidocyclazocine Analogues: Redefining the Structure-Activity . . . " Biorg. Med. Chem. Ltrs. 11, 623-626 (2001).
Davies et al. "Palladium catalysed elaboration of codeine and morphine" J. Chem. Soc., Perkin Trans. 1, 1413-1420 (2001).
McCurdy et al., Investigation of Phenolic Bioisosterism in Opiates: 3-Sulfonamido . . . Org. Lett. 2, 819-821 (2000).
Kubota et al. "Synthesis and Biological Activity of 3-Substituted . . . " Bior. Med. Chem. Ltrs. 8, 799-804 (1998).
Wentland et al. "8-Aminocyclazocine Analogues: Synthesis and Structure . . . " Bior. Med. Chem. Ltrs. 10, 183-187 (2000).
Wentland et al. "Selective Protection and Functionalization of Morphine . . . " J. Med. Chem. 43, 3558-3565 (2000).
Danso-Danquah et al. "Synthesis and σ Binding Properties of 2'-Substituted . . . " J. Med. Chem. 38, 2978-2985 (1995).
Coop et al, "δ Opioid Affinity and Selectivity of 4-Hydroxy-3-methoxyindolomorphianan Analogues Related to Naltrindole", J. Med. Chem. 42, 1673-1679 (1999).
Kubota et al. "Palladium-Catalyzed Cyanation of Hindered, Electron-Rich . . . " Tetrahedron Ltrs. 39, 2907-2910 (1998).
Nan et al., Sumthesis pf2'-Amino-17-cyclopropylmethyl-6,7-dehydro-3,14-dihydroxy-4,5α-eposy-6,7:4',5'-thiazolomorphinan from Naltrexone[1], J. Heterocyclic Chem. 34, 1195-1203 (1997).
Coop et al, "Direct and Simple Conversion of Codeine to Thebainone-A and Dihydrothebainone", Heterocycles, 50, 39-42 (1999).
Neumeyer, et al, "Design and Synthesis of Novel Dimeric Morphinan Ligands for κ and μ Opioid Receptors", J. Med. Chem. 46, 5162-5170 (2003).

*Primary Examiner*—Charanjit S. Aulakh
(74) *Attorney, Agent, or Firm*—Heslin Rothenberg Farley & Mesiti P.C.

(57) ABSTRACT

4-Hydroxybenzomorphans containing carboxamide or thiocarboxamide at the 3-position are useful as analgesics, anti-diarrheal agents, anticonvulsants, antitussives and anti-addiction medications.

8 Claims, No Drawings

4-HYDROXYBENZOMORPHANS

CROSS REFERENCE TO RELATED APPLICATION

This application claims priority from U.S. Provisional Application 60/625,348 filed Nov. 5, 2004, the entire disclosure of which is incorporated herein by reference.

STATEMENT AS TO RIGHTS UNDER FEDERALLY-SPONSORED RESEARCH

This invention was made with Government support under Contract No. R01DA12180, awarded by the National Institutes of Health. Accordingly, the U.S. Government has certain rights in this invention.

FIELD OF THE INVENTION

The invention relates to 4-hydroxybenzomorphans substituted at the 3-position with carboxamide or thiocarboxamide. The compounds are useful as analgesics, anti-diarrheal agents, anticonvulsants, antitussives, anti-cocaine, and anti-addiction medications.

BACKGROUND OF THE INVENTION

Opiates have been the subject of intense research since the isolation of morphine in 1805, and thousands of compounds having opiate or opiate-like activity have been identified. Many opioid receptor-interactive compounds including those used for producing analgesia (e.g., morphine) and those used for treating drug addiction (e.g., naltrexone and cyclazocine) have been employed in human therapy. Almost all therapeutically useful opioids in the benzazocine and morphinane classes have a phenolic hydroxyl group (OH) at a position which is numbered "8" in the numbering system used for 2,6-methano-3-benzazocines [e.g., cyclazocine and EKC (ethylketocyclazocine)] and which is numbered "3" in the numbering system used for morphinanes (e.g., morphine).

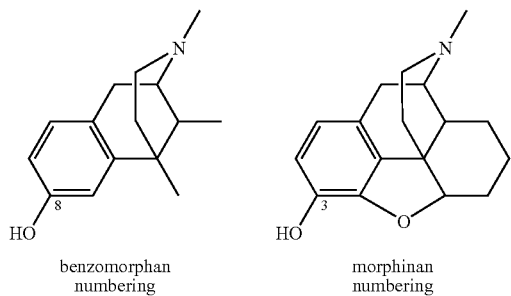

benzomorphan numbering     morphinan numbering

Although the compounds of the present invention do not possess the furan ring of the morphinans, the morphinan numbering system will be used:

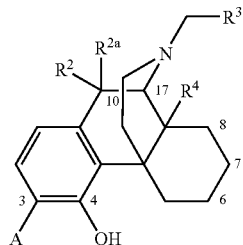

2,6-Methano-3-benzazocines are also known as benzomorphans, and this terminology will be used interchangeably herein.

Until the publications of Wentland et al., [BioOrg. Med. Chem. Lett. 11, 623–626 (2001) and BioOrg. Med. Chem. Lett. 11, 1717–1721 (2001)] the uniform experience in the art of the past seventy years had been that removal or replacement of the phenolic 3-hydroxy group had led to pharmacologically inactive compounds.

SUMMARY OF THE INVENTION

We have now found that when the 3-hydroxyl group is replaced by a number of small, polar, neutral residues, such as carboxamide and thiocarboxamide groups, the adjacent 4-position may be substituted with a hydroxyl to produce compounds with an extraordinary affinity for the opioid receptor. The compounds of the invention are therefore useful as analgesics, anti-pruritics, anti-diarrheal agents, anticonvulsants, antitussives, anorexics, and anti-obesity drugs and as treatments for hyperalgesia, drug addiction, respiratory depression, dyskinesia, pain (including neuropathic pain), irritable bowel syndrome and gastrointestinal motility disorders.

In one aspect, the invention relates to compounds of formula I:

A compound of formula:

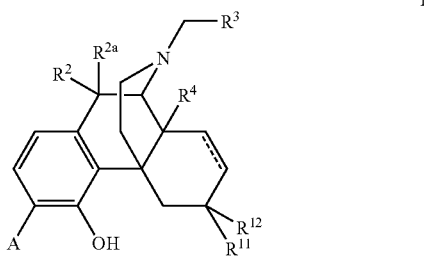

I wherein

A is chosen from —C(═O)NH$_2$ and —C(═S)NH$_2$;

$R^2$ and $R^{2a}$ are both hydrogen or taken together $R^2$ and $R^{2a}$ are ═O;

$R^3$ is chosen from hydrogen, lower alkyl, alkenyl, aryl, heterocyclyl, benzyl and hydroxyalkyl;

$R^4$ is chosen from hydrogen, hydroxy, amino, lower alkoxy, $C_1$-$C_{20}$ alkyl and $C_1$-$C_{20}$ alkyl substituted with hydroxy or carbonyl;

$R^{11}$ is hydrogen;

$R^{12}$ is chosen from hydrogen, hydroxy, lower alkoxy and —$NR^{13}R^{14}$; or together, $R^{11}$ and $R^{12}$ form a carbonyl or a vinyl substituent;

$R^{13}$ and $R^{14}$ are chosen independently from hydrogen and $C_1$ to $C_7$ hydrocarbon;

and the dotted line represents an optional double bond.

In another aspect, the invention relates to methods for treating a disease or condition by altering a response mediated by an opioid receptor. The method comprises bringing a compound of formula I into contact with an opioid receptor. Diseases and conditions that are amenable to therapy with the compounds of the invention include pain, pruritis, diarrhea, irritable bowel syndrome, gastrointestinal motility disorder, obesity, respiratory depression, convulsions, coughing, hyperalgesia and drug addiction. Drug addiction, as used herein, includes alcohol, nicotine, opiate and cocaine addiction. There is evidence in the literature that the compounds may also be useful as immunosuppressants and antiinflammatories and for reducing ischemic damage (and cardioprotection), for improving learning and memory, and for treating urinary incontinence.

DETAILED DESCRIPTION OF THE INVENTION

From many years of SAR studies, it is known that the hydroxyl of morphinans and benzomorphans interacts with a specific site in the opiate receptor. Previous exploration of the tolerance of this site for functional groups other than phenolic hydroxyls has almost uniformly resulted in the complete or near-complete loss of opioid binding. We have earlier reported (WO 02/36573) that the hydroxyl could be replaced with one of several bioisosteres. Although a fairly wide range of primary and secondary carboxamides, as well as carboxylates, aminomethyl, hydroxymethyl and even dihydroimidazolyl exhibited binding in the desired range below 25 nanomolar, optimal activity was observed with a carboxamido, thiocarboxamido, hydroxyamidino or formamido group. We have now found that benzomorphans having a hydroxyl at 4 and the bioisostere "A" at position 3 have a surprising level of opioid activity.

The phenolic 3-hydroxyl functionality of benzomorphans and morphinans can be chemically converted to an amide by a simple, flexible and convenient route described in WO 02/36573 and in WO 2004/007449, and thiocarboxamido, hydroxyamidino and formamido compounds are also easily synthesized as described in those publications. Preferred residues A are —C(=O)NH$_2$ and —C(=S)NH$_2$.

It is known in the art that compounds that are μ, δ and κ agonists exhibit analgesic activity; compounds that are selective μ agonists exhibit anti-diarrheal activity and are useful in treating dyskinesia; μ antagonists and κ agonists are useful in treating heroin, cocaine, alcohol and nicotine addiction; κ agonists are also anti-pruritic agents and are useful in treating hyperalgesia. In general, the dextrorotatory isomers of morphinans are useful as antitussives and anticonvulsants.

Exemplary opioid receptor ligands having known high affinity are shown in the following Chart.

Replacement of

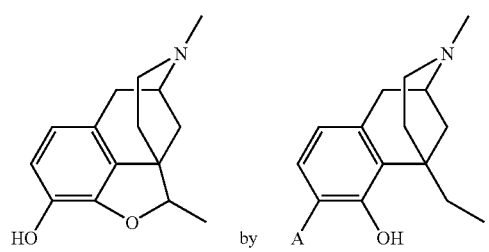

in the compounds of the Chart produces compounds that exhibit strong affinity for opioid receptors.

Chart. Opioid Receptor Ligands
Morphine and Morphinans

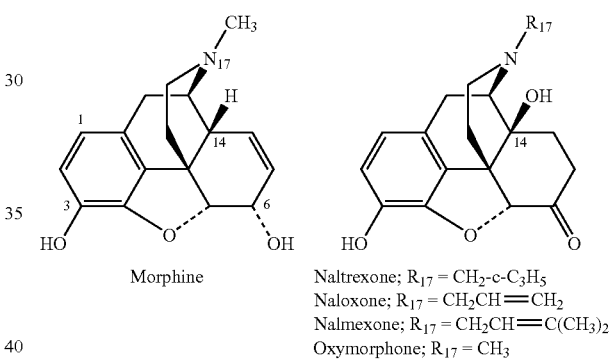

Morphine

Naltrexone; $R_{17}$ = $CH_2$-c-$C_3H_5$
Naloxone; $R_{17}$ = $CH_2CH$=$CH_2$
Nalmexone; $R_{17}$ = $CH_2CH$=$C(CH_3)_2$
Oxymorphone; $R_{17}$ = $CH_3$

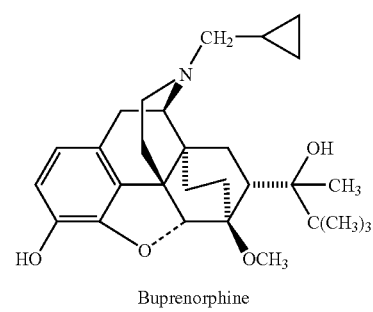

Buprenorphine

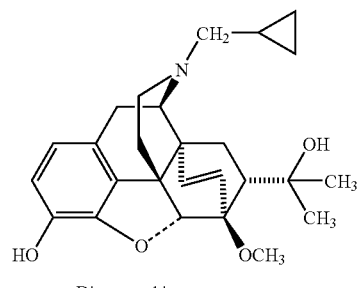

Diprenorphine
Etorphine (N-Me; n-Pr vs Me)

-continued

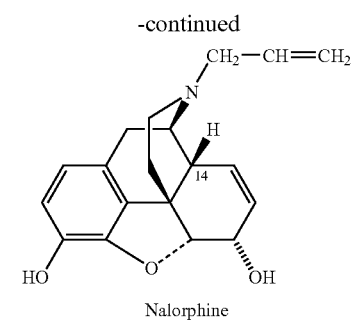
Nalorphine

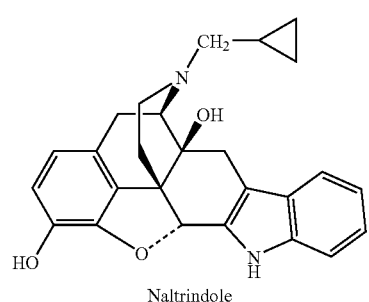
Naltrindole

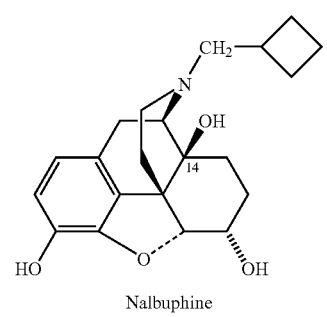
Nalbuphine

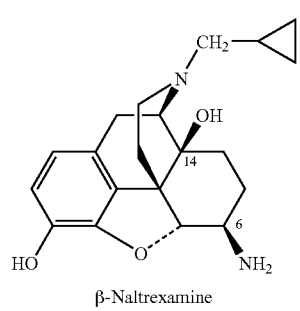
β-Naltrexamine

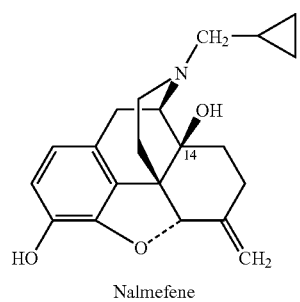
Nalmefene

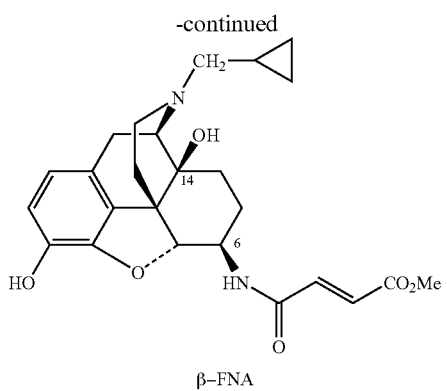
β-FNA

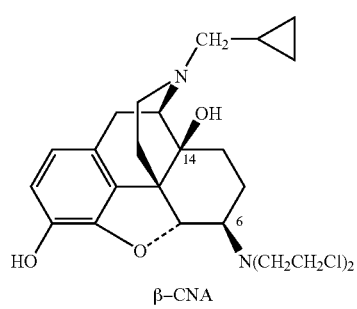
β-CNA

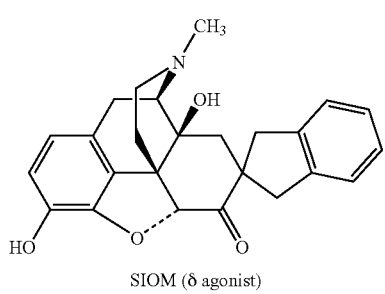
SIOM (δ agonist)

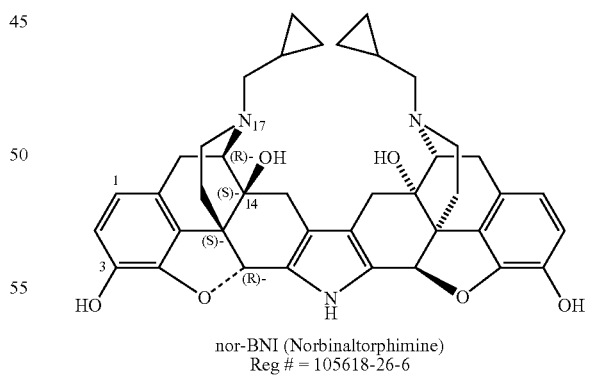
nor-BNI (Norbinaltorphimine)
Reg # = 105618-26-6

Other opioid receptors are reported in Aldrich, J. V. "Analgesics" in *Burger's Medicinal Chemistry and Drug Discovery*, M. E. Wolff ed., John Wiley & Sons 1996, pages 321–44, the disclosures of which are incorporated herein by reference.

The affinities of the compounds of the invention are determined by the method described in Wentland et al.-

[*BioOrg. Med. Chem. Lett.* 9. 183–187 (2000)]. Antinociceptive activity is evaluated by the method described in Jiang et al. [*J. Pharmacol. Exp. Ther.* 264, 1021–1027 (1993), page 1022] or by the method described in Neumeyer et al. [*J. Med. Chem.* 46, 5162 (2003). We have examined the receptor binding of compounds of formula I in a series of analogs of known compounds in which the OH is replaced by the A group and a hydroxyl is introduced adjacent the A group. The data is shown in Tables 1, 2, 3, and 4. Data for the standards used are also shown in the tables. The results of these in vitro tests are accepted by persons of skill in the art as predictive of therapeutic utility in vivo.

TABLE I

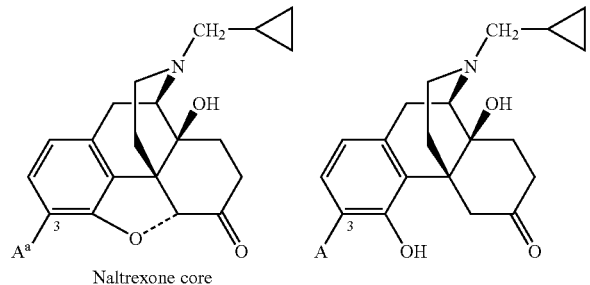

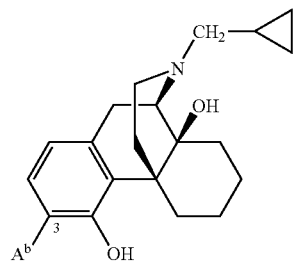

Naltrexone series
$K_i$ (nM ± S.E.)

| Sample | A or $A^a$ or $A^b$ | [$^3$H]DAMGO (μ) | [$^3$H]Naltrindole (δ) | [$^3$H]U69,593 (κ) |
|---|---|---|---|---|
| 1 | $A^a$ = —OH (naltrexone) | 0.17 ± 0.03 | 11 ± 1.1 | 0.31 ± 0.03 |
| 2 | $A^a$ = —CONH$_2$ | 1.9 ± 0.21 | 110 ± 8.1 | 22 ± 0.85 |
| 3 | A = —CONH$_2$ | 0.052 ± 0.004 | 2.6 ± 0.26 | 0.23 ± 0.018 |
| 4 | A = —OCH$_3$ | 6.7 ± 0.46 | >10 μM | 12 ± 0.29 |
| 26 | A = —CSNH$_2$ | 1.2 ± 0.093 | 140 ± 11 | 5.0 ± 0.72 |
| 24 | $A^b$ = —CONH$_2$ | 0.16 ± 0.011 | 4.2 ± 0.74 | 0.29 ± 0.015 |

TABLE II

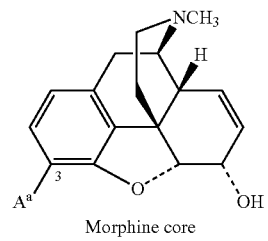

Morphine core

Morphine series
$K_i$ (nM ± S.E.)

| Sample | $A^a$ | [$^3$H]DAMGO (μ) | [$^3$H]Naltrindole (μ) | [$^3$H]U69,593 (κ) |
|---|---|---|---|---|
| 5 | $A^a$ = —OH (morphine) | 0.88 ± 0.14 | 140 ± 18 | 24 ± 2.3 |
| 6 | $A^a$ = —CONH$_2$ | 34 ± 1.8 | 1900 ± 81 | 2000 ± 97 |

TABLE III

Oxymorphone derivatives

Oxymorphone series
K<sub>i</sub> (nM ± S.E.)

| Sample | A | [$^3$H]DAMGO (μ) | [$^3$H]Naltrindole (δ) | [$^3$H] U69,593 (κ) |
|---|---|---|---|---|
| 7 | A = —OCH$_3$ 7,8-dehydro | 15 ± 0.33 | 2000 ± 80 | 740 ± 25 |
| 8 | A = —OCH$_3$ 7,8-dihydro | 4.6 ± 0.65 | 1200 ± 65 | 350 ± 8.5 |

TABLE IV

Nalbuphine core

Nalbuphine series
K$_i$ (nM ± S.E.)

| Sample | A or A$^a$ or A$^b$ or A$^c$ | [$^3$H]DAMGO (μ) | [$^3$H]Naltrindole (δ) | [$^3$H]U69,593 (κ) |
|---|---|---|---|---|
| 10 | A$^a$ = —OH (nalbuphine) | 1.6 ± 0.37 | 580 ± 80 | 3.0 ± 0.63 |
| 11 | A$^a$ = —CONH$_2$ | 3.8 ± 0.62 | 150 ± 82 | 0.46 ± 0.04 |
| 21 | A = —CONH$_2$ | 0.13 ± 0.0083 | 4.2 ± 0.36 | 0.27 ± 0.013 |
| 22a | A$^b$ = —CONH$_2$ | 0.52 ± 0.014 | 78 ± 7.0 | 9.0 ± 1.9 |
| 22b | A$^c$ = —CONH$_2$ | 0.072 ± 0.008 | 3.9 ± 0.42 | 0.34 ± 0.05 |

Definitions

Throughout this specification the terms and substituents retain their definitions.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, cyclopropyl, butyl, s-and t-butyl, cyclopropyl, cyclobutyl and the like. Preferred alkyl groups are those of C20 or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Aryl and heteroaryl mean a 5- or 6-membered aromatic or heteroaromatic ring containing 0–3 heteroatoms selected from O, N, or S; a bicyclic 9- or 10-membered aromatic or heteroaromatic ring system containing 0–3 heteroatoms selected from O, N, or S; or a tricyclic 13- or 14-membered aromatic or heteroaromatic ring system containing 0–3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl, phenethyl and the like. Heteroarylalkyl means an alkyl residue attached to a heteroaryl ring. Examples include, e.g., pyridinylmethyl, pyrimidinylethyl and the like.

Heterocycle means a cycloalkyl or aryl residue in which one to two of the carbons is replaced by a heteroatom such as oxygen, nitrogen or sulfur. Heteroaryls form a subset of heterocycles. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like.

Substituted alkyl, aryl, cycloalkyl, or heterocyclyl refer to alkyl, aryl, cycloalkyl, or heterocyclyl wherein up to three H atoms in each residue are replaced with halogen, hydroxy, loweralkoxy, carboxy, carboalkoxy, carboxamido, cyano, carbonyl, —NO2, —NR1R2; alkylthio, sulfoxide, sulfone, acylamino, amidino, phenyl, benzyl, heteroaryl, phenoxy, benzyloxy, heteroaryloxy, or substituted phenyl, benzyl, heteroaryl, phenoxy, benzyloxy, or heteroaryloxy.

Virtually all of the compounds described herein contain one or more asymmetric centers and may thus give rise to enantiomers, diastereomers, and other stereoisomeric forms that may be defined, in terms of absolute stereochemistry, as $(R)^{13}$ or $(S)^-$. The present invention is meant to include all such possible isomers, as well as their racemic and optically pure forms. In general it has been found that the levo isomer of morphinans and benzomorphans is the more potent antinociceptive agent, while the dextro isomer may be useful as an antitussive or antispasmodic agent. Optically active $(R)^-$ and $(S)^-$ isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, and as would be understood by the person of skill in the medical art, to which the invention pertains, the recitation of the compound includes pharmaceutically acceptable salts, hydrates, solvates, clathrates, and polymorphs. The term "pharmaceutically acceptable salt" refers to salts prepared from pharmaceutically acceptable non-toxic acids or bases including inorganic acids and bases and organic acids and bases. Salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. The term "solvate" refers to a compound—in this case eszopiclone—in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The term "preventing" as used herein refers to administering a medicament beforehand to forestall or obtund an attack. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. The term "treating" includes prophylaxis as well as the amelioration of the acute symptoms. Note that "treating" refers to either or both of the amelioration of symptoms and the resolution of the underlying condition. In many of the conditions of the invention, the administration of the opioid may act not directly on the disease state, but rather on some pernicious symptom, and the improvement of that symptom leads to a general and desirable amelioration of the disease state.

Although this invention is susceptible to embodiment in many different forms, preferred embodiments of the invention are shown. It should be understood, however, that the present disclosure is to be considered as an exemplification of the principles of this invention and is not intended to limit the invention to the embodiments illustrated. It may be found upon examination that certain members of the claimed genus are not patentable to the inventors in this application. In this event, subsequent exclusions of species from the compass of applicants' claims are to be considered artifacts of patent prosecution and not reflective of the inventors' concept or description of their invention; the invention encompasses all of the members of the genus I that are not already in the possession of the public.

Abbreviations
The following abbreviations and terms have the indicated meanings throughout:
Ac=acetyl
AcOH=acetic acid
BNB=4-bromomethyl-3-nitrobenzoic acid
Boc=t-butyloxy carbonyl
Bu=butyl
c-=cyclo
DAMGO=Tyr-ala-Gly-NMePhe-NHCH$_2$OH
DBU=diazabicyclo[5.4.0]undec-7-ene
DCM=dichloromethane=methylene chloride=CH$_2$Cl$_2$
DEAD=diethyl azodicarboxylate
DIC=diisopropylcarbodiimide
DIEA=N,N-diisopropylethyl amine
DMAP=4-N,N-dimethylaminopyridine DMF=N,N-dimethylformamide
DMSO=dimethyl sulfoxide
DPPF=1,1'-bis(diphenylphosphino)ferrocene
DVB=1,4-divinylbenzene
EEDQ=2-ethoxy-1-ethoxycarbonyl-1,2-dihydroquinoline
Et$_3$N=triethylamine
EtOAc=ethyl acetate
Fmoc=9-fluorenylmethoxycarbonyl
GC=gas chromatography
HATU=O-(7-Azabenzotriazol-1-yl)-1,1,3,3-tetramethyluronium hexafluorophosphate
HOBt=hydroxybenzotriazole
Me=methyl
mesyl=methanesulfonyl
MTBE=methyl t-butyl ether
NMO=N-methylmorpholine oxide
PEG=polyethylene glycol
Ph=phenyl
PhOH=phenol
PhN(Tf)$_2$ N-phenyltrifluoromethanesulfonimide
PfP=pentafluorophenol
PPTS=pyridinium p-toluenesulfonate
PyBroP=bromo-tris-pyrrolidino-phosphonium hexafluorophosphate
rt=room temperature
sat'd=saturated
s-=secondary
t-=tertiary
Tf=triflate, CF$_3$SO$_2$O—
TBDMS=t-butyldimethylsilyl
TFA=trifluoroacetic acid
THF=tetrahydrofuran
TMOF=trimethyl orthoformate
TMS=trimethylsilyl
tosyl=p-toluenesulfonyl
Trt=triphenylmethyl

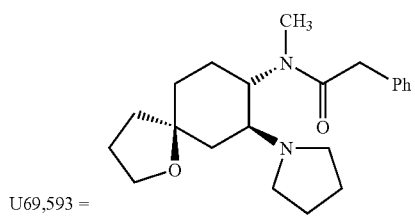

U69,593 =

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group that is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as *Protective Groups in Organic Synthesis* by T. W. Greene [John Wiley & Sons, New York, 1991], which is incorporated herein by reference.

The following examples illustrate the syntheses of various compounds of the present invention having formula I, many of which are found in the Tables. The remaining compounds listed in the Tables were prepared in a similar fashion. Furthermore, the invention is not limited to the compounds prepared in the examples or found in the Tables, and similar procedures may be used to prepare additional compounds having formula I.

Unless indicated otherwise, the reactants and reagents used in the examples are readily available materials. Such materials can be conveniently prepared in accordance with conventional preparatory procedures or obtained from commercial sources. $^1$H NMR multiplicity data are denoted by s (singlet), d (doublet), t (triplet), q (quartet), m (multiplet), and br (broad).

EXAMPLE 1

Synthesis of 3-Carboxyamido-4-hydroxy-naltrexone derivative 3

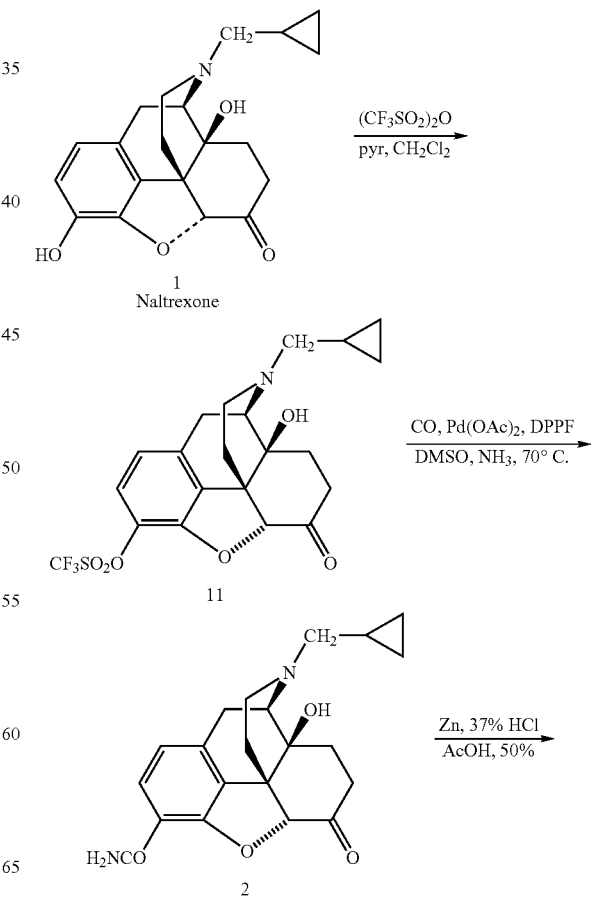

-continued

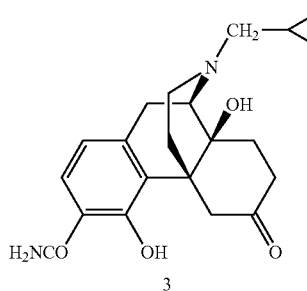
3

(A) Synthesis of 3-Carboxyamido-naltrexone 2

The triflate 11 of naltrexone was prepared according to the method of Wentland et al. (*Bioorg. Med. Chem. Lett.* 9, 183–187 (2000)), and the carboxamide 2 was prepared by the method described by Wentland et al. [(*Bioorg. Med. Chem. Lett.* 11, 623–626 (2001); and *Bioorg. Med. Chem. Lett.* 11, 1717–1721 (2001)] involving Pd-catalyzed carbonylation of the triflate 11 in the presence of ammonia and the Pd(0) ligand, DPPF ([1,1'-bis(diphenylphosphino)ferrocene]) and DMSO.

(B) Synthesis of 3-Carboxyamido-4-hydroxy-naltrexone derivative 3

Zinc dust (26 mg, 0.40 mmol) was added in portions to a solution of 2 (50 mg, 0.14 mmol) in HCl (37%, 0.2 mL) and AcOH (2 mL) at reflux. After heating at reflux for a further 15 min, the reaction was cooled by the addition of ice/water (10 mL) and basified (pH=9) with $NH_3/H_2O$, and the solution was extracted with EtOAc (3×10 mL). The organic extracts were washed with brine, dried, and concentrated. The residue was purified by column chromatography ($SiO_2$, $CH_2Cl_2$, $CH_3OH$: $NH_3/H_2O$=15:1:0.01) to give compound 3 as a foam (25 mg, 50%). $^1$H NMR ($CDCl_3$) δ13.28(s, 1H, 4-OH), 7.15(d, 1H, J=8.1, H-2), 6.47(d, 1H, J=8.4, H-1), 6.10(br, 1H, N—H), 4.35(br, 1H, N—H), 4.04(dd, 1H, J=1.8, 13.5, H-5), 3.11(d, 1H, J=6), 2.99(d, 1H, J=5.7), 2.94(s, 1H), 2.86(d, 1H, J=6), 2.84–2.75(m, 2H), 2.65–2.61 (m, 2H), 2.17–2.05(m, 1H), 1.89–1.84(m, 1H), 0.56–0.50 (m, 2H), 0.13–0.09(m, 2H). $[α]_D^{25}$=−98.4° (c=0.6, $CH_2Cl_2$). MS m/z (ESI) 371 (MH$^+$).

EXAMPLE 2

Synthesis of 3-Methoxy-4-hydroxy-naltrexone derivative 4

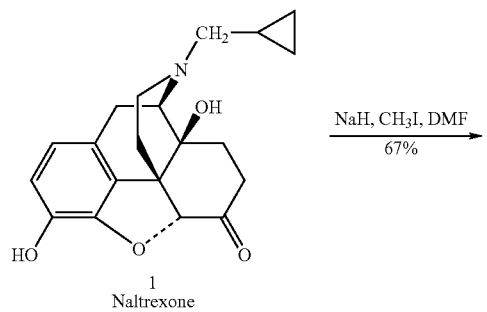
1
Naltrexone

NaH, CH$_3$I, DMF
───────────→
67%

-continued

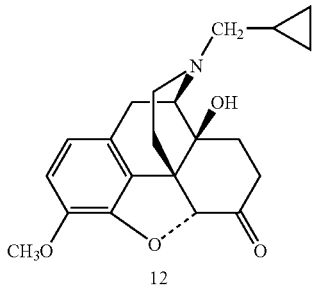
12

Zn, 37% HCl
───────────→
70%

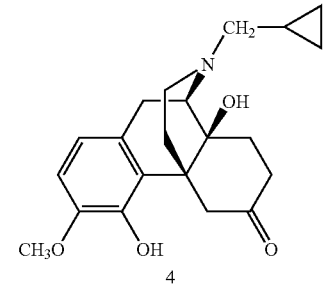
4

(A) Synthesis of 3-Methoxy-naltrexone derivative 12

Using the procedure of Nan et al., *J. Heterocyclic Chem.* 34, 1195–1203 (1997), 95% sodium hydride (22 mg, 0.87 mmol) was added to a solution of naltrexone 1 (200 mg, 0.58 mmol) in dry DMF (1 mL) at room temperature. After stirring for 15 min, the solution was cooled to 5° C. in an ice bath and methyl iodide (40 µl, 99 mg, 0.70 mmol) was added. After stirring for another 15 min the reaction solution was concentrated in vacuo. The residue was purified by flash chromatography ($SiO_2$, $CH_2Cl_2$: $NH_3/H_2O$=100:1) to give derivative 12 as a foam (131 mg, 67%). $^1$H NMR ($CDCl_3$) δ6.69(d, 1H, J=8.0, H-2), 6.61(d, 1H, J=8.0, H-1), 4.67(s, 1H, H-5), 3.89(3H, 3-OCH$_3$), 3.18(m, 1H), 3.06(m, 2H), 2.99(s, 1H), 2.87(s, 1H), 2.70(m, 1H), 2.59(m, 1H), 2.40(m, 2H), 2.41(m, 2H), 2.31(m, 2H), 2.12(m, 2H), 1.89(m, 2H), 1.59(m, 1H), 0.87(m, 1H), 0.55(m, 2H), 0.15(m, 2H). $[α]_D^{25}$=−181.7° (c=0.12, $CH_2Cl_2$). MS m/z (ESI) 356 (MH$^+$).

(B) Synthesis of 3-methoxy-4-hydroxy-naltrexone derivative 4

A modification of a known procedure Coop et al., *J. Med. Chem.* 42, 1673–1679 (1999) was used in this preparation. Zinc dust (114 mg, 1.72 mmol) was added in portions to a solution of derivative 12 (122 mg, 0.34 mmol) in HCl (37%, 0.2 mL) and AcOH (2 mL) at reflux. After heating at reflux for a further 15 min, the reaction was cooled by the addition of ice/water (20 mL) and basified (pH=9) with $NH_3/H_2O$, and the solution was extracted with EtOAc (3×10 mL). The organic extracts were washed by brine, dried, and concentrated. The residue was purified by column chromatography ($SiO_2$, $CH_2Cl_2$: $CH_3OH$: $NH_3/H_2O$=20:1:0.01) to give compound 4 as a foam (85 mg, 70%). $^1$H NMR ($CDCl_3$) δ6.67(d, 1H, J=8.0, H-2), 6.56(d, 1H, J=8.0, H-1), 6.12(s, 1H, 4-OH), 3.94(d, 1H, J=13.0), 3.82(s 3H, 3-OCH$_3$), 3.10(m, 1H), 2.97(m, 1H), 2.80(m, 2H), 2.61(m, 1H), 2.36(m, 2H), 2.15

(m, 1H), 2.05(m, 2H), 1.82(m, 1H), 0.54(m, 2H), 0.12(m, 2H). [α]$_D$$^{25}$=−96.2° (c=0.5, CH$_2$Cl$_2$). MS m/z (ESI) 358 (MH$^+$).

EXAMPLE 3

Synthesis of 3-Methoxy-4-hydroxy-6-oxo-morphine derivative 7

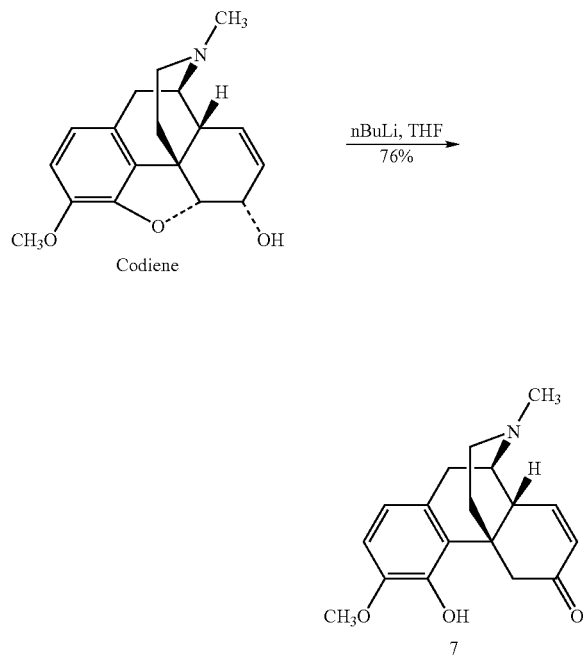

Using the procedure of Coop et al. (*J. Med. Chem.* 42, 1673–1679 (1999); and *Heterocycles* 50, 39–42 (1999)), n-butyllithium (1.52 M in hexane, 1.6 mL, 2.50 mmol) was added to a solution of codeine (150 mg, 0.501 mmol) in THF at −78° C. After stirring at −78° C. for 1 h, the slight yellow solution was warmed to room temperature and then stirred for 20 min. The reaction was quenched with water (10 mL). The mixture was extracted with CHCl$_3$ three times. The combined organic phases were washed with brine, dried over sodium sulfate, filtered, and concentrated to give a solid residue, which was purified by flash chromatography (CH$_2$Cl$_2$:MeOH:NH$_4$OH 15:1:0.1) to give dehydro compound 7 as a white foam (114 mg, 0.381 mmol, 76%): $^1$H NMR (500 MHz, CDCl$_3$) δ6.68 (dd, 1H, J=10.0, 2.0 Hz), 6.64 (d, 1H, J=8.0 Hz), 6.55 (d, 1H, J=8.5 Hz), 6.00 (bs, 1H), 5.89 (dd, 1H, J=10.0, 3.0 Hz), 4.26 (d, 1H, J=15.5 Hz), 3.81 (s, 3H), 3.22 (m, 1H), 3.02 (d, 1H, J=18.5 Hz), 2.89 (s, 1H), 2.65 (m, 1H), 2.54 (m, 1H), 2.43 (s, 3H), 2.38(d, 1H, J=15.0 Hz), 2.07 (m, 1H), 1.90 (m, 2H); $^{13}$C NMR (125 MHz, CDCl$_3$) δ 199.38, 149.53, 144.91, 144.58, 130.75, 130.18, 122.86, 118.10, 108.71, 55.93, 55.80, 48.88, 47.02, 46.95, 42.52, 40.47, 36.19, 24.32; MS (ESI) m/z 300 (M+H)$^+$; Anal. Calcd. for C$_{18}$H$_{21}$NO$_3$.0.5H$_2$O: C, 70.11; H, 7.19; N, 4.54. Found: C, 69.94; H 6.87; N, 4.38.

EXAMPLE 4

Synthesis of 3-Methoxy-4-hydroxy-6-oxo-7,8-dihydro-morphine derivative 8

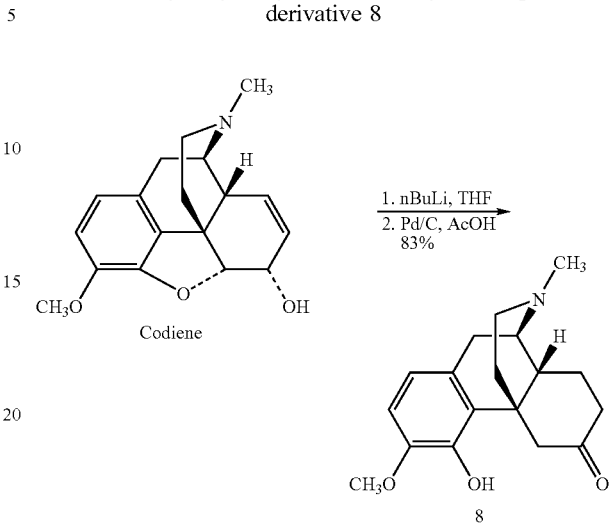

n-Butyllithium (1.52 M in hexane, 1.6 mL, 2.50 mmol) was added to a solution of codeine (150 mg, 0.501 mmol) in THF at −78° C. After stirring at −78° C. for 1 h, the slight yellow solution was warmed to room temperature and then stirred for 20 min. The reaction was quenched with water (10 mL). The mixture was extracted with CHCl$_3$ three times. The combined organic phases were washed with brine, dried over sodium sulfate, filtered, and concentrated to give a solid residue, which was dissolved in AcOH (10 mL) and stirred with 10% Pd/C (54 mg) under hydrogen atmosphere (30 psi) for 20 h. The reaction mixture was filtered and concentrated to give an off-white residue, which was purified by flash chromatography (CH$_2$Cl$_2$:MeOH:NH$_4$OH 14:1:0.1) to give compound 8 as a white solid (125 mg, 0.415 mmol, 83%): $^1$H NMR (500 MHz, CDCl$_3$) δ6.67 (d, 1H, J=8.0 Hz), 6.60 (d, 1H, J=8.0 Hz), 6.09 (s, 1H), 4.23 (dd, 1H, J=13.5, 2.5 Hz), 3.83 (s, 3H), 2.98 (d, 1H, J=18.5 Hz), 2.66 (m, 1H), 2.44 (m, 2H), 2.42 (s, 3H), 2.24 (m, 3H), 2.06 (m, 1H), 1.86 (m, 3H), 1.69 (m, 2H); MS (ESI) m/z 302 (M+H)$^+$; Anal. Calcd. for C$_{18}$H$_{23}$NO$_3$–$_{0.5}$H$_2$O: C, 69.65; H, 7.79; N, 4.51. Found: C, 70.04; H, 7.68; N, 4.39.

EXAMPLE 5

Synthesis of 3-Carboxyamido-4-hydroxy-hydrocodone derivative 17

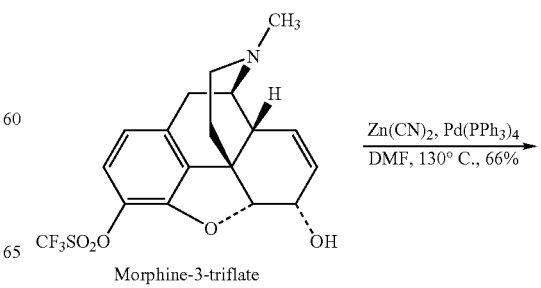

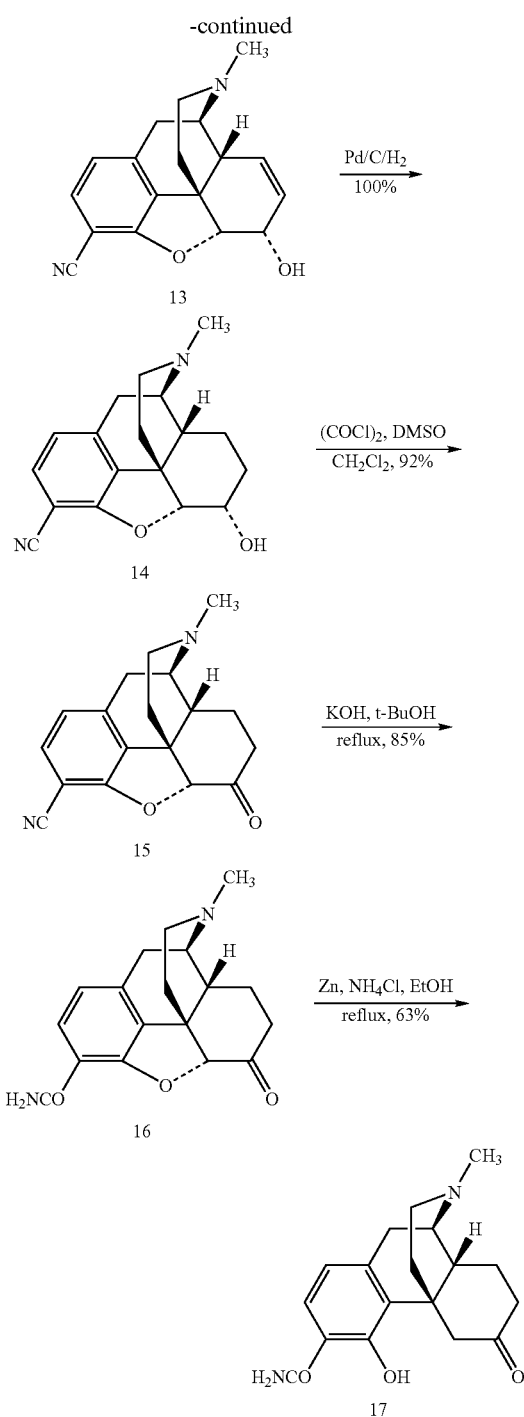

(A) Synthesis of Morphine-3-carbonitrile derivative 13

Morphine-3-triflate was prepared according to the procedure described by Wentland et al. (*J. Med. Chem.* 3, 3558–3565 (2000)) and was then added (420 mg, 1.007 mmol) to a dry flask along with zinc cyanide (354 mg, 3.022 mmol), and tetrakis(triphenylphosphine)palladium(0) (116 mg, 0.101 mmol) under nitrogen atmosphere. The flask was then equipped with a condenser, sealed with a septum, and vacuumed/back-filled with argon for 5 cycles. Dry DMF (2.0 mL) was added via syringe and the resulting mixture was stirred for 20 h at 120° C. The reaction was then cooled to 25° C., diluted with EtOAc (30 mL), washed once with saturated bicarbonate solution, twice with water, and once with brine. The organic phase was dried over sodium sulfate, filtered, and concentrated to give a solid residue, which was purified by flash chromatography ($CH_2Cl_2$:MeOH:$NH_4OH$ 30:1:0.1) to give 13 as a white solid (195 mg, 0.663 mmol, 66%): $^1$H NMR (500 MHz, $CDCl_3$) δ7.20 (d, 1H, J=8.1 Hz), 6.68 (d, 1H, J=8.1 Hz), 5.71 (m, 1H), 5.30 (m, 1H), 5.02 (m, 1H), 4.24 (bs, 1H), 3.38 (m, 1H), 3.12 (d, 1H, J=19.8 Hz), 2.68 (m, 3H), 2.44 (s, 3H), 2.33 (m, 2H), 2.10 (m, 1H), 1.85 (m, 1H); MS (ESI) m/z 295 (M+H)$^+$; Anal. Calcd. for $C_{18}H_{18}N_2O_2 \cdot 0.125H_2O$: C, 72.89; H, 6.20; N, 9.44. Found: C, 72.74; H, 6.14; N, 9.28.

(B) Synthesis of 7,8-Dihydro-morphine-3-carbonitrile derivative 14

A solution of compound 13 (81 mg, 0.28 mmol) and 10% Pd/C in 5 mL MeOH was hydrogenated under the pressure of 40 psi. for 4 h at room temperature. The reaction mixture was filtered with celite, and the solvent was removed to provide 14 as a foam (81 mg; 100%). $^1$HNMR($CDCl_3$) δ7.20(d,1H, J=8.1 Hz), 6.69(d,1H, J=8.1 Hz), 4.7(s,1H), 3.12–3.09(m, 1H), 3.0(d, 1H, J=19.5 Hz), 2.55(m, 1H 1H), 2.4(m,1H), 2.35(s,3H), 2.25(m, 2H), 2.1(dd, 1H, J=4.2, 12.0), 1.94–1.84(m, 2H), 1.55(m, 1H), 1.4(m, 1H)). $[\alpha]_D^{25}$=−50.6° (c=0.64, $CH_2Cl_2$). MS m/s (ESI) 297(MH$^+$).

(C) Synthesis of Hydrocodone-3-carbonitrile derivative 15

Oxalyl chloride (41.9 µl, 0.47 mmol) was dissolved in 1 mL anhydrous $CH_2Cl_2$ under argon at −78° C. Dry DMSO (66.9 µl, 0.95 mmol) was then added. The reaction mixture stirred for 5 min and a solution of 14 (70 mg, 0.24 mmol) in 1 mL dry $CH_2Cl_2$ was added by syringe. The mixture stirred for 20 min at −78° C. and 164 µl Et$_3$N was added to the reaction mixture and warmed to room temperature. The mixture was partitioned between water (10 mL) and $CH_2Cl_2$ (10 mL×3). The combined organic solvent was dried (MgSO$_4$), then concentrated in vacuo. The resulting compound was purified by flash column (silica gel, $CH_2Cl_2$:$CH_3OH$:NH$_3$/H$_2$O=20:1:0.01) to give 63.7 mg (92%) of 15 as a foam. $^1$HNMR($CDCl_3$) δ7.28(d,1H, J=8.1 Hz), 6.84(d, 1H, J=8.1 Hz), 4.83(s,1H), 3.24(t, 1H,J=2.4 Hz), 3.1(d, 1H, J=19.5 Hz), 2.66(m, 1H), 2.61(dt, 2H, J=2.4, 5.7 Hz), 2.46(m, 1H), 2.44(s, 3H), 2.33(m, 1H), 2.1(m, 1H), 1.92–1.87(m, 1H), 1.75 (m, 1H), 1.18(m, 1H)). $[\alpha]_D^{25}$=−64.4° (c=0.87, $CH_2Cl_2$). MS m/z (ESI) 295(MH$^+$).

(D) Synthesis of 3-Carboxyamido-hydrocodone derivative 16

A solution of 15 (72 mg, 0.25 mmol) and KOH in t-BuOH (10 mL) was heated at reflux and stirred for 2 h. After cooling, the reaction mixture was filtered with celite, and the filtrate was concentrated. The residue was purified by flash column (silica gel, $CH_2Cl_2$:$CH_3OH$:NH$_3$/H$_2$O=20:1:0.01) to give 64.9 mg (85%) of 16 as a foam. $^1$HNMR($CDCl_3$) δ7.77(d,1H, J=8.1 Hz) δ7.46(s, 1H), 6.82(d,1H, J=8.1 Hz), 5.89(s, 1H), 4.80(s,1H), 3.2(dd, 1H, J=2.7,6.0 Hz), 3.1(d, 1H, J=19.5 Hz), 2.66(m, 1H), 2.62(m, 2H), 2.46(m,1H), 2.44(s,3H), 2.33(d, 1H, J=5.4 Hz), 2.1(m, 1H), 1.92–1.87(m, 1H), 1.75(m, 1H), 1.18(m, 1H)). $[\alpha]_D^{25}$=−96.60 (c=0.23, $CH_2Cl_2$). MS m/z (ESI) 313(MH$^+$).

(E) Synthesis of 3-Carboxyamido-4-hydroxy-hydrocodone derivative 17

A mixture of 16 (46 mg, 0.15 mmol), NH$_4$Cl (78.9 mg, 0.88 mmol), zinc dust (57.3 mg, 0.88 mmol) and EtOH (95%, 15 mL) was heated at reflux for 4 h. After cooling, the mixture was filtered, and the solids were washed with NH$_3$/H$_2$O (2 mL). The combined filtrates and the washings were concentrated and extracted with CH$_2$Cl$_2$ (10 mL×3). The organic extracts were dried (MgSO$_4$) and concentrated. The residue was purified by column chromatography (SiO$_2$, CH$_2$Cl$_2$:CH$_3$OH:NH$_3$/H$_2$O=10:1:0.01) to give 29 mg (63%) of 17 as a foam. $^1$H NMR (CDCl$_3$) 613.1(s, 1H), 7.12(dd, 1H, J=1.2, 8.1 Hz) δ7.46(s, 1H), 6.54(d,1H, J=8.1 Hz), 6.02(br, 2H), 4.35(d,1H, J=13.5 Hz), 2.99(m, 2H), 2.92(m, 1H), 2.77(dd, 1H, J=4.7, 13.9 Hz), 2.46(m, 2H), 2.4(s,3H), 2.24(m, 2H), 1.98(m, 1H), 1.87(m, 1H), 1.6(m,1H)). $[\alpha]_D^{25}$=−25.90 (c=0.7, CHCl$_3$). MS m/z (ESI) 315(MH$^+$).

EXAMPLE 6

Synthesis of 3-Carboxamido-4-hydroxy-6α-hydroxy-nalbuphine derivative 22a and 3-Carboxamido-4-hydroxy-6 β-hydroxy-nalbulphine derivative 22b

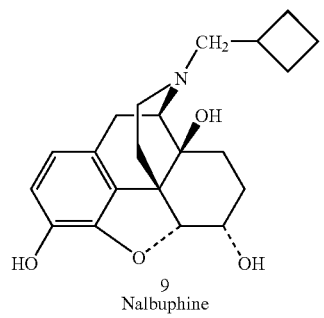

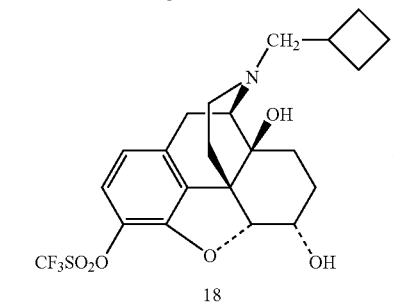

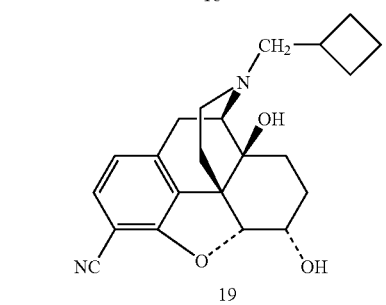

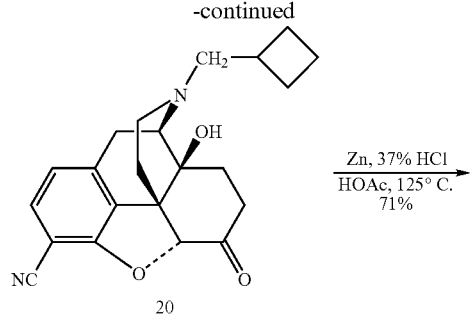

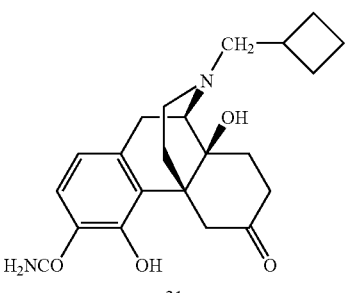

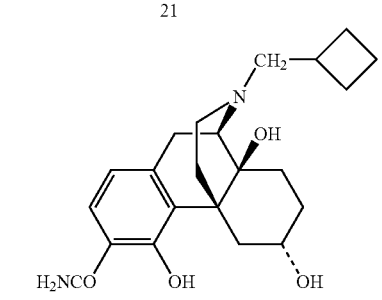

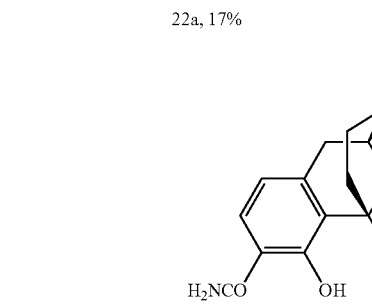

(A) Synthesis of Nalbuphine-3-triflate 18

To a dispersion of nalbuphine hydrochloride (714 mg, 1.812 mmol) in CH$_2$Cl$_2$ (30 mL) was added triethylamine (630 μL, 4.53 mmol) at 0° C., followed by PhN(Tf)$_2$ (654 mg, 1.812 mmol) in one portion. The mixture was allowed to warm to room temperature and stirred overnight. The solvent was removed under reduced pressure, and the residue was partitioned between 6 N NH$_4$OH solution (50 mL) and CH$_2$Cl$_2$ (3×50 mL). The CH$_2$Cl$_2$ extracts were combined and the volume was reduced to 50 mL under reduced pressure. The organic phase was washed with saturated aqueous Na$_2$CO$_3$ solution (3×50 mL), then dried (Na$_2$SO$_4$) and concentrated to give 18 (886 mg, 1.812 mmol, 100%). $^1$H NMR (500 MHz, CDCl$_3$) δ 6.95 (d, 1H, J=8.5 Hz), 6.69 (d, 1H, J=8.5 Hz), 4.97 (broad, 1H), 4.75 (d, 1H, J=5.0 Hz), 4.19 (m, 1H), 3.12 (d, 1H, J=19.0 Hz), 2.85 (d, 1H, J=6.0

Hz), 2.66 (dd, 1H, J=19.0, 6.0 Hz), 2.52–2.44 (m, 4H), 2.25 (td, 1H, J=12.5, 5.0 Hz), 2.17 (td, 1H, J=12.5, 3.0 Hz), 2.07 (m, 1H), 1.98–1.81 (m, 3H), 1.73–1.44 (m, 5H), 1.26 (m, 1H); $^{13}$C NMR (125 MHz, CDCl$_3$) δ 149.5, 134.4, 134.3, 130.2, 121.8, 119.6, 92.9, 69.8, 66.6, 62.7, 60.8, 47.0, 43.4, 33.8, 32.8, 27.6, 27.1, 26.9, 23.8, 23.7, 18.9; MS (ESI) m/z 490 (M+H)$^+$.

(B) Synthesis of Nalbuphine-3-carbonitrile derivative 19

To a three-neck flask equipped with a condenser was added compound 18 (886 mg, 1.812 mmol), Zn(CN)$_2$ (638 mg, 5.436 mmol) and Pd(PPH$_3$)$_4$ (419 mg, 0.362 mmol) under nitrogen atmosphere. The flask was sealed and removed from the glove box. Anhydrous DMF (6 mL) was injected through the septum. The mixture was heated at 135° C. for 24 hours. DMF was removed under reduced pressure, and the residue was partitioned between saturated aqueous NaHCO$_3$ solution (100 mL) and ethyl acetate (3×100 mL). The organic extracts were combined, dried (Na$_2$SO$_4$) and concentrated to give crude product, which was purified by flash chromatography [(hexane/ethyl acetate/ammonium hydroxide (1:1:0.01)] to give compound 19 as a while foam (549 mg, 1.50 mmol, 83%). $^1$H NMR (500 MHz, CDCl$_3$) δ 7.25 (d, 1H, J=8.0 Hz), 6.73 (d, 1H, J=8.0 Hz), 4.77 (d, 1H, J=5.0 Hz), 4.23 (m, 1H), 3.15 (d, 1H, J=19.5 Hz), 2.86 (d, 1H, J=6.0 Hz), 2.69 (dd, 1H, J=19.5, 6.0 Hz), 2.49 (m, 4H), 2.26 (td, 1H, J=13.0, 5.0 Hz), 2.15 (td, 1H, J=11.5, 3.0 Hz), 2.06 (m, 3H), 1.90 (m, 1H), 1.84 (m, 2H), 1.65 (m, 3H), 1.47 (m, 1H), 1.41 (m, 1H), 1.18 (m, 1H); $^{13}$C NMR (125 MHz, CDCl$_3$) δ 161.3, 139.8, 131.7, 131.3, 119.1, 115.8, 92.5, 90.4, 69.5, 66.4, 62.3, 60.6, 46.1, 43.0, 33.5, 32.8, 27.7, 26.9, 26.7, 24.2, 23.4, 18.7; MS (ESI) m/z 367 (M+H)$^+$ (C) Synthesis of 6-Oxo-nalbuphine-3-carbonitrile derivative 20

Oxalyl chloride (143 µL, 1.64 mmol) in CH$_2$Cl$_2$ (5 mL) was cooled to −78° C. under nitrogen atmosphere and anhydrous DMSO (232 µL, 3.27 mmol) was added via a syringe. After 2 minutes, compound 19 (335 mg, 0.915 mmol) in dry CH$_2$Cl$_2$ (5 mL) was added, and the stirring was continued for 15 minutes. Dry triethylamine (570 µL, 4.097 mmol) was added, and the stirring was continued for 5 minutes. After warmed to room temperature, the reaction mixture was partitioned between saturated aqueous NaHCO$_3$ solution (50 mL) and CH$_2$Cl$_2$ (3×50 mL). The combined organic layer was washed with brine (100 mL), dried (Na$_2$SO$_4$) and concentrated to give crude product, which was purified by flash chromatography [CH$_2$Cl$_2$/MeOH (25:1)] to give compound 20 (308 mg, 0.846 mmol, 92%). $^1$H NMR (500 MHz, CDCl$_3$) δ 7.28 (d, 1H, J=8.0 Hz), 6.80 (d, 1H, J=8.0 Hz), 5.13 (broad, 1H), 4.81 (s, 1H), 3.19 (d, 1H, J=19.5 Hz), 3.03 (td, 1H, J=14.5, 6.0 Hz), 2.97 (d, 1H, J=6.0 Hz), 2.67 (dd, 1H, J=19.5, 6.0 Hz), 2.60–2.48 (m, 4H), 2.44 (td, 1H, J=12.5, 5.5 Hz), 2.32 (m, 1H), 2.16–2.02 (m, 6H), 1.70 (m, 2H), 1.53 (m 2H); $^{13}$C NMR (125 MHz, CDCl$_3$) δ 206.2, 159.2, 138.8, 132.0, 129.4, 119.5, 115.0, 92.7, 91.2, 69.8, 62.2, 60.3, 50.0, 43.2, 35.9, 33.5, 31.2, 30.6, 26.9, 26.7, 24.0, 18.7; MS (ESI) m/z 365 (M+H)$^+$.

(D) Synthesis of 3-Carboxamido-4-hydroxy-6-oxo-nalbuphine derivative 21

To a flask containing compound 20 (252 mg, 0.692 mmol) was added Zn dust (900 mg, 13.85 mmol), glacial acetic acid (5 mL) and concentrated HCl (0.69 mL, 8.3 mmol). After refluxing at 125° C. for 3 hours, the reaction mixture was cooled to 0° C. and concentrated NH$_4$OH solution was added to adjust pH to 10. The slurry mixture was extracted with CH$_2$Cl$_2$ (3×100 mL). The organic extracts were combined, dried (Na$_2$SO$_4$) and concentrated to yield 253 mg crude product. Flash chromatography gave compound 21 (187 mg, 0.487 mmol, 71%). $^1$H NMR (500 MHz, CDCl$_3$) δ 13.14 (s, 1H), 7.13 (d, 1H, J=8.0 Hz), 6.56 (d, 1H, J=8.0 Hz), 6.30–5.40 (broad, 2H), 4.65 (s, 1H), 4.04 (dd, 1H, J=11.0, 2.0 Hz), 3.02 (m, 1H) 2.94 (d, 1H, J=13.0 Hz), 2.89 (m, 1H), 2.86 (m, 1H), 2.50 (m, 3H), 2.45 (m, 1H), 2.16–1.71 (m, 9H), 1.68 (m, 3H); $^{13}$C NMR (125 MHz, CDCl$_3$) δ 212.5, 173.3, 162.0, 144.3, 127.2, 124.9, 117.5, 111.0, 68.9, 60.4, 59.9, 45.6, 44.7, 43.9, 37.7, 33.8, 32.7, 32.1, 27.0, 26.8, 26.7, 18.7; IR (film) ν$_{max}$ 3354, 2928, 1709, 1653, 1617, 1429 cm$^{-1}$; MS (ESI) m/z 385 (M+H)$^+$.

(E) Synthesis of 3-Carboxamido-4-hydroxy-6α-hydroxy-nalbuphine derivative 22a and 3-Carboxamido-4-hydroxy-6 β-hydroxy-nalbuphine derivative 22b Compound 21 (115 mg, 0.3 mmol) was dissolved in MeOH (2 mL) and cooled to 0° C. NaBH$_4$ (46 mg, 1.2 mmol) was added in one portion. The reaction was stirred at 0° C. for two hours and quenched by the addition of saturated aqueous NH$_4$Cl solution. MeOH was removed under reduced pressure, and concentrated NH$_4$OH solution was added to adjust pH to 10. The aqueous phase was extracted with CHCl$_3$ (4×50 mL), and the organic extracts were combined, dried (NaSO$_4$) and concentrated to yield 97 mg crude product. Flash chromatography [CHCl$_3$/MeOH/NH$_4$OH (10:1:0.1)] gave isomers 22a (31.8 mg, 0.082 mmol, 17%) and 22b (40.7 mg, 0.105 mmol, 35%). 22a: $^1$H NMR (500 MHz, CDCl$_3$) δ 13.43 (s, 1H,), 7.12 (d, 1H, J=8.0 Hz), 6.62 (d, 1H, J=8.0 Hz), 6.30–5.30 (broad, 2H 4.60 (s, 1H), 4.18 (s, 1H), 3.47 (m, 1H), 3.01 (d, 1H, J=19.0 Hz), 2.95 (td, 1H, J=19.0, 6.0 Hz), 2.66 (d, 1H, J=5.5 Hz), 2.47–2.37 (m, 4H), 2.10–1.85 (m, 10H), 1.66–1.47 (m, 4H), 1.27 (m, 1H); $^{13}$C NMR (125 MHz, CDCl$_3$) δ 173.6, 161.9, 144.3, 131.4, 123.9, 118.4, 110.5, 69.5, 67.8, 60.8, 60.4, 44.4, 39.5, 35.2, 33.7, 33.1, 27.7, 27.00, 26.96, 26.93, 26.7, 18.7; IR (film) ν$_{max}$ 3445 (broad), 2929, 1653, 1425 cm$^{-1}$; MS (ESI) m/z 387 (M+H)$^+$. 22b: $^1$H NMR (500 MHz, CDCl$_3$) δ 13.10 (s, 1H,), 7.15 (d, 1H, J=8.0 Hz), 6.60 (d, 1H, J=8.0 Hz), 6.30–5.30 (broad, 2H 4.46 (s, 1H), 3.53 (m, 1H), 3.38 (m, 1H), 3.00 (d, 1H, J=19.5 Hz), 2.84 (td, 1H, J=19.5, 6.5 Hz), 2.71 (d, 1H, J=6.0 Hz), 2.46–2.38 (m, 4H), 2.07–1.49 (m, 14H), 1.34 (d, 1H, J=5.0 Hz); $^{13}$C NMR (125 MHz, CDCl$_3$) δ 173.6, 161.0, 143.9, 127.5, 124.5, 117.2, 110.3, 68.5, 66.7, 59.7, 59.6, 43.6, 41.4, 37.3, 33.1, 31.6, 29.8, 29.7, 26.2, 25.9 (2C), 17.8; IR (film) ν$_{max}$ 3410 (broad), 2929, 1653, 1617, 1425 cm$^{-1}$; MS (ESI) m/z 387 (M+H)$^+$.

EXAMPLE 7

Synthesis of 3-Carboxamide-4-hydroxy-naltrexone derivative 24

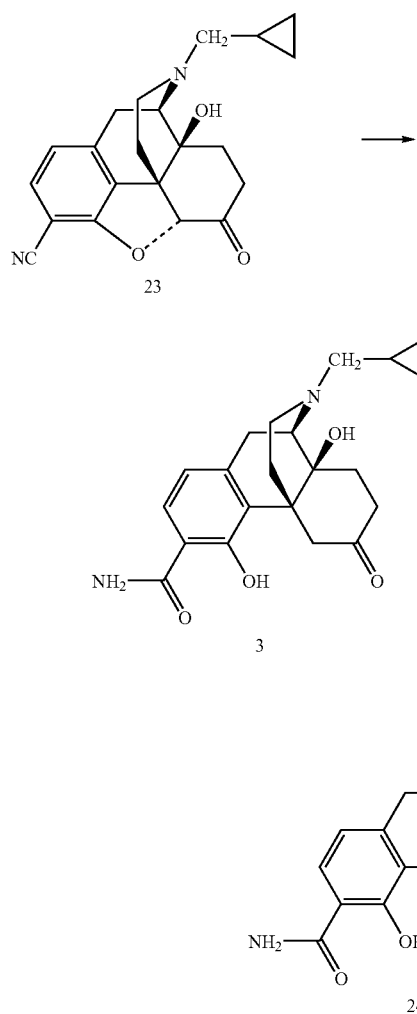

To a 50 mL of flask containing nitrile 23 (made using the procedure of Kubota et al., *Tetrahedron Letters* 39(19), 2907–2910 (1998)) (452 mg, 1.29 mmol) was added 325 mesh zinc dust (1679 mg, 25.83 mmol), followed by the addition of 8 mL of glacial acetic acid and 1.29 mL of 12 M HCl. A condenser was installed and the reaction mixture was then refluxed at 125° C. for 3 h. Some zinc balls formed at the bottom of the flask. The reaction was cooled to 0° C. and concentrated $NH_4OH$ was added dropwise to adjust the pH to about 10. Formation of a white slurry was observed. The mixture was extracted with methylene chloride (100 mL×3). The organic phases were dried over sodium sulfate and concentrated to give a light yellow foam (484 mg), which was purified using flash chromatography (25:1:0.1 $CH_2Cl_2$: MeOH:$NH_4OH$) to give 3 as a white foam (264 mg, 0.713 mmol, 55%) and 24 as a white solid (100 mg, 0.281 mmol, 22%): mp 268–270° C.; $^1H$ NMR (500 MHz, $CDCl_3$) 12.99 (s, 1H), 7.15 (d, 1H, J=8.0 Hz), 6.60 (d, 1H, J=8.0 Hz), 6.60–5.40 (bs, 2H), 4.52 (bs, 1H), 3.11 (m, 1H), 3.00–2.80 (m, 3H), 2.60 (m, 1H), 2.31 (m, 2H), 2.10–1.70 (m, 4H), 1.60–1.35 (m, 5H), 1.18 (m, 1H), 0.83 (m, 1H), 0.50 (m, 2H), 0.10 (m, 2H); MS (ESI) m/z 300 (M+H)$^+$; Anal. Calcd. for $C_{21}H_{28}N_2O_3 \cdot 0.375H_2O$: C, 69.44; H, 7.98; N, 7.71. Found: C, 69.46; H, 8.11; N, 7.42. $[\alpha]^{25}_D = -85.0°$ (c=0.40, $CHCl_3$).

EXAMPLE 8

Synthesis of 3-Thiocarboxyamido-4-hydroxy-naltrexone Derivative 26

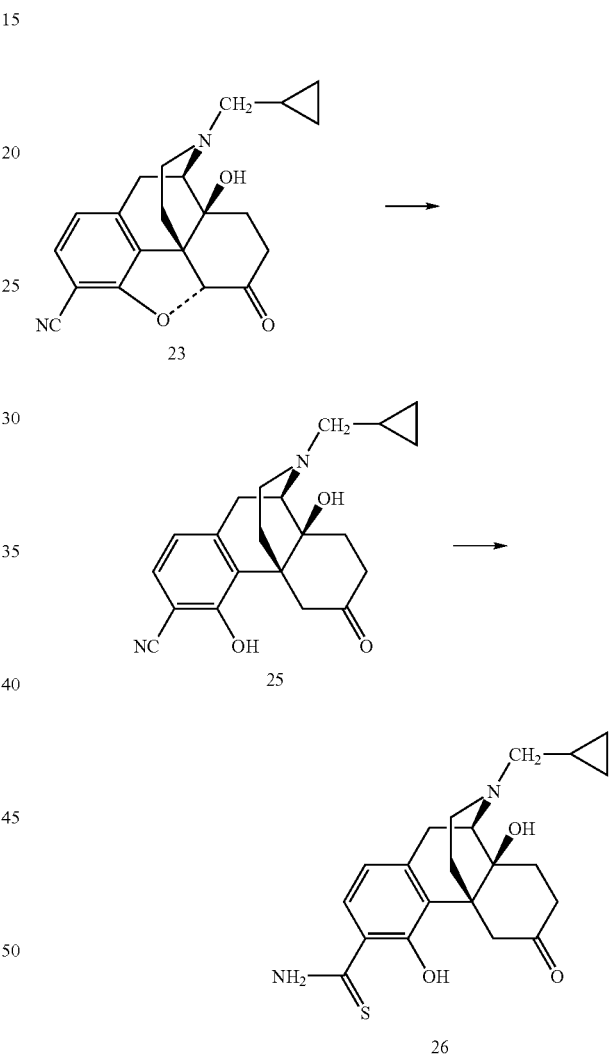

(A) Synthesis of 3-Carbonitrile-4-hydroxy-naltrexone derivative 25

To a 50 mL of flask containing nitrile 23 (101 mg, 0.28 mmol) was added 325 mesh zinc dust (126 mg, 1.94 mmol) and ammonia hydrochloride (148 mg, 2.77 mmol), followed by 4 mL of EtOH:$H_2O$ (20:1). A condenser was installed and the reaction mixture was then refluxed at 95° C. for 3 h. The reaction was cooled to room temperature and filtered through a cake of celite. The celite was washed with MeOH.

The filtrates were concentrated and then partitioned between CH$_2$Cl$_2$ (40 mL×3) and 40 mL of NH$_4$OH in water (pH 8–9). The organic phases were combined, dried over sodium sulfate and concentrated to give a solid (106 mg), which was purified using flash chromatography (25:1:0.1 CH$_2$Cl$_2$: MeOH:NH$_4$OH) to give 25 as a white solid (63 mg, 0.17 mmol, 62%). $^1$H NMR (500 MHz, CDCl$_3$) δ7.25 (d, 1H, J=9.3 Hz), 7.40 (d, 1H, J=7.8 Hz), 5.12 (bs, 1H), 3.81 (d, 1H, J=12.6 Hz), 3.40–2.60 (m, 6H), 2.41 (s, 2H), 2.30–1.75 (m, 5H), 1.60 (m, 1H), 0.88(m, 1H), 0.56 (m, 2H), 0.14 (m, 2H); MS (ESI) m/z 300 (M+H)$^+$; [α]$^{25}_D$=−64.3 (c=0.56°, EtOH).

(B) Synthesis of 3-Thiocarboxyamido-4-hydroxy-naltrexone derivative 26

A mixture of nitrile 25 (49 mg, 0.139 mmol) and O,O-diethyl-dithiophosphoric acid (475 μL, 2.78 mmol) in water (2 mL) and ethanol (4 mL) was heated at 80° C. for 22 h. The reaction mixture was cooled to room temperature and partitioned between saturated NaHCO$_3$ (20 mL) and CH$_2$Cl$_2$ (20 mL×3). The organic phases were dried over sodium sulfate and concentrated to give 26 as a yellow solid (56 mg), which was purified using flash chromatography (40:1: 0.1 EtOAc:MeOH:NH$_4$OH) to give a yellow foam (36 mg, 0.093 mmol, 67%). $^1$H NMR (500 MHz, CDCl$_3$) δ12.24 (s, 1H), 7.20–7.06 (m, 3H), 6.59 (d, 1H, J=8.5 Hz), 4.72 (bs, 1H), 4.02 (d, 1H, J=14.0 Hz), 3.14 (m, 1H), 2.94 (m, 2H), 2.94–2.70 (m, 2H), 2.65 (m, 1H), 2.20–1.70 (m, 6H), 0.87 (m, 1H), 0.55 (m, 2H), 0.12 (m, 2H); MS (ESI) m/z 300 (M+H)$^+$; Anal. Calcd. for C$_{21}$H$_{26}$N$_2$O$_3$S 0.25H$_2$O: C, 64.51; H, 6.83; N, 7.16. Found: C, 64.50; H, 6.61; N, 6.94. [α]$^{25}_D$=+85.0° (c=0.20, CHCl$_3$).

Each of the patents, patent applications, and references mentioned herein is hereby incorporated by reference in its entirety.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

I claim:

1. A compound of formula:

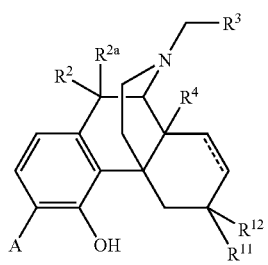

wherein
A is chosen from —C(=O)NH$_2$ and —C(=S)NH$_2$;
R$^2$ and R$^{2a}$ are both hydrogen or taken together R$^2$ and R$^{2a}$ are =O;
R$^3$ is chosen from hydrogen, lower alkyl, alkenyl, aryl, heterocyclyl, benzyl and hydroxyalkyl;
R$^4$ is chosen from hydrogen, hydroxy, amino, lower alkoxy, C$_1$–C$_{20}$ alkyl and C$_1$–C$_{20}$ alkyl substituted with hydroxy or carbonyl;
R$^{11}$ is hydrogen;
R$^{12}$ is chosen from hydrogen, hydroxy, lower alkoxy and —NR$^{13}$R$^{14}$; or
together, R$^{11}$ and R$^{12}$ form a carbonyl or a vinyl substituent;
R$^{13}$ and R$^{14}$ are chosen independently from hydrogen and C$_1$ to C$_7$ hydrocarbon; and
the dotted line represents an optional double bond.

2. A compound according claim 1 wherein
R$^2$ and R$^{2a}$ are hydrogen;
R$^3$ is chosen from hydrogen, cyclopropyl, and cyclobutyl, vinyl and tetrahydrofuranyl;
R$^4$ is chosen from hydrogen and hydroxyl;
R$^{11}$ is hydrogen;
R$^{12}$ is chosen from hydrogen and hydroxy; or
together, R$^{11}$ and R$^{12}$ form a carbonyl.

3. A compound according to claim 1 of formula:

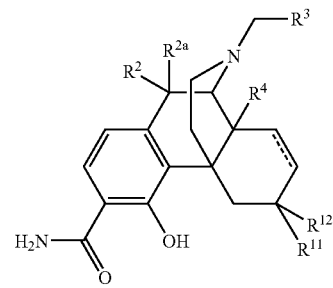

wherein
R$^2$ and R$^{2a}$ are both hydrogen or taken together R$^2$ and R$^{2a}$ are =O;
R$^3$ is chosen from hydrogen, lower alkyl, alkenyl, aryl, heterocyclyl, benzyl and hydroxyalkyl;
R$^4$ is chosen from hydrogen, hydroxy, amino, lower alkoxy, C$_1$–C$_{20}$ alkyl and C$_1$–C$_{20}$ alkyl substituted with hydroxy or carbonyl;
R$^{11}$ is hydrogen;
R$^{12}$ is chosen from hydrogen, hydroxy, lower alkoxy and —NR$^{13}$R$^{14}$; or
together, R$^{11}$ and R$^{12}$ form a carbonyl or a vinyl substituent;
R$^{13}$ and R$^{14}$ are chosen independently from hydrogen and C$_1$ to C$_7$ hydrocarbon; and
the dotted line represents an optional double bond.

4. A compound according to claim 3 wherein:
R$^2$ and R$^{2a}$ are hydrogen;
R$^3$ is chosen from hydrogen, cyclopropyl, and cyclobutyl, vinyl and tetrahydrofuranyl;
R$^4$ is chosen from hydrogen and hydroxyl;
R$^{11}$ is hydrogen;
R$^{12}$ is chosen from hydrogen and hydroxy; or
together, R$^{11}$ and R$^{12}$ form a carbonyl.

5. A compound according to claim 4 selected from the group of

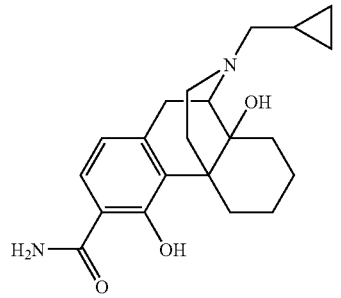

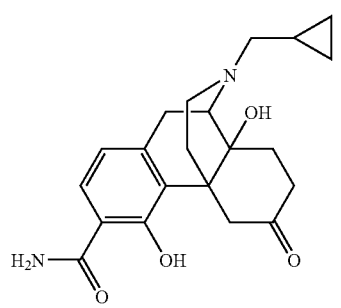

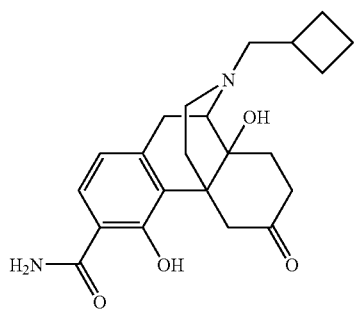

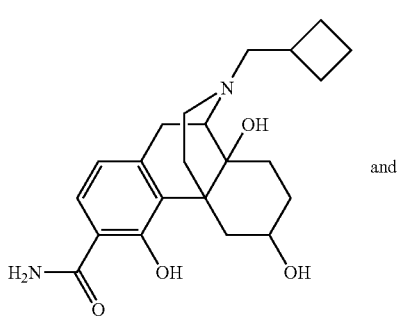

and

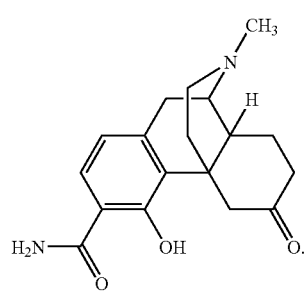

6. A compound according to claim 1 of formula:

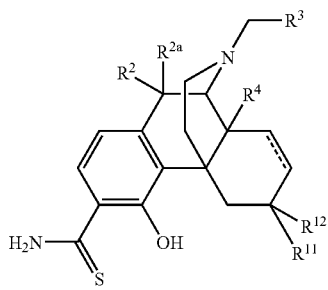

wherein
- $R^2$ and $R^{2a}$ are both hydrogen or taken together $R^2$ and $R^{2a}$ are =O;
- $R^3$ is chosen from hydrogen, lower alkyl, alkenyl, aryl, heterocyclyl, benzyl and hydroxyalkyl;
- $R^4$ is chosen from hydrogen, hydroxy, amino, lower alkoxy, $C_1$–$C_{20}$ alkyl and $C_1$–$C_{20}$ alkyl substituted with hydroxy or carbonyl;
- $R^{11}$ is hydrogen;
- $R^{12}$ is chosen from hydrogen, hydroxy, lower alkoxy and —$NR^{13}R^{14}$; or
- together, $R^{11}$ and $R^{12}$ form a carbonyl or a vinyl substituent;
- $R^{13}$ and $R^{14}$ are chosen independently from hydrogen and $C_1$ to $C_7$ hydrocarbon; and
- the dotted line represents an optional double bond.

7. A compound according to claim 6 wherein:
- $R^2$ and $R^{2a}$ are hydrogen;
- $R^3$ is chosen from hydrogen, cyclopropyl, and cyclobutyl, vinyl and tetrahydrofuranyl;
- $R^4$ is chosen from hydrogen and hydroxyl;
- $R^{11}$ is hydrogen;
- $R^{12}$ is chosen from hydrogen and hydroxy; or
- together, $R^{11}$ and $R^{12}$ form a carbonyl.

8. The compound of formula

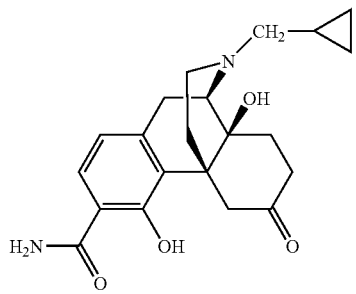

according to claim 5.

* * * * *